(12) United States Patent
Huddart et al.

(10) Patent No.: US 7,306,205 B2
(45) Date of Patent: Dec. 11, 2007

(54) HUMIDIFICATION SYSTEM

(75) Inventors: Brett John Huddart, Auckland (NZ); Scott Robert Mackie, Cambridge (GB); Craig Karl White, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 261 days.

(21) Appl. No.: 10/524,062

(22) PCT Filed: Aug. 29, 2003

(86) PCT No.: PCT/NZ03/00193

§ 371 (c)(1),
(2), (4) Date: Sep. 22, 2005

(87) PCT Pub. No.: WO2004/020031

PCT Pub. Date: Mar. 11, 2004

(65) Prior Publication Data

US 2006/0113690 A1    Jun. 1, 2006

(30) Foreign Application Priority Data

Aug. 30, 2002  (NZ) ...................... 521107

(51) Int. Cl.
*B01F 3/04* (2006.01)
(52) U.S. Cl. .............. 261/130; 261/137; 261/30; 128/203.14; 128/203.25; 128/203.26
(58) Field of Classification Search ............ 261/129, 261/130, 131, 135, 137, 142, 30, 119.1; 128/203.14, 128/203.25, 203.26, 203.27, 204.14
See application file for complete search history.

(56) References Cited

U.S. PATENT DOCUMENTS

| 5,445,143 | A | 8/1995 | Sims | |
|---|---|---|---|---|
| 5,640,951 | A | 6/1997 | Huddart et al. | |
| 2001/0050080 | A1* | 12/2001 | Seakins et al. | 128/203.16 |
| 2002/0078733 | A1* | 6/2002 | Seakins et al. | 73/29.02 |
| 2004/0060558 | A1* | 4/2004 | Gradon et al. | 128/203.26 |
| 2004/0074493 | A1* | 4/2004 | Seakins et al. | 128/203.16 |
| 2004/0102731 | A1* | 5/2004 | Blackhurst et al. | 604/26 |

FOREIGN PATENT DOCUMENTS

| AU | 2612092 | 4/1993 |
|---|---|---|
| DE | 4226995 | 2/1994 |
| GB | 2338420 | 12/1999 |
| JP | 2001-129090 | 5/2001 |
| NZ | 507553 | 7/2003 |
| WO | WO 01/13981 | 3/2001 |

* cited by examiner

*Primary Examiner*—Scott Bushey
(74) *Attorney, Agent, or Firm*—Trexler, Bushnell, Giangiorgi, Blackstone & Marr, Ltd.

(57) ABSTRACT

Breathing assistance apparatus including humidifier (4) and heated conduit (6) adapted to deliver humidified gases at desired and accurate level of humidity to patient. Humidifier includes controller (18) that delivers flow rate, temperature and humidity of gases and then determines required power input to deliver gases as required. Need for external sensors is dispensed with providing simple and less bulky apparatus.

22 Claims, 3 Drawing Sheets

HUMIDIFICATION SYSTEM

BACKGROUND OF THE INVENTION

1. Field of the Invention

This invention relates to a humidification system, particularly but not solely, for supplying optimal humidity temperature of gases to a patient to assist the patient's breathing for ventilation purposes, or for the supply of gases for other medical procedures, such as laparoscopic, endoscopic or ophthalmic procedures.

2. Summary of the Prior Art

A number of methods are known in the art for assisting a patient's breathing. Continuous Positive Airway pressure or CPAP involves the administration of air under pressure to a patient, usually by a nasal mask. It is used in the treatment of snoring and Obstructive Sleep Apnea (OSA), a condition characterised by repetitive collapse of the upper airway during inspiration. Positive pressure splints the upper airway open, preventing its collapse. Treatment of OSA with nasal CPAP has proven to be both effective and safe, but CPAP is difficult to use and the majority of patients experience significant side effects, particularly in the early stages of treatment.

Upper airway symptoms adversely affect treatment with CPAP. Mucosal drying is uncomfortable and may awaken patients during the night. Rebound nasal congestion commonly occurs during the following day, simulating a viral infection. If untreated, upper airway symptoms adversely affect rates of use.

Gases may also be supplied to patients suffering from Chronic Obstructive Pulmonary Disease (COPD). Also, at present there is no suitable means for home humidification of tracheotomy patients. These patients have by-passed upper airways and are prone to infection and congestion.

A number of methods may be employed to treat such symptoms, including pharmacological agents to reduce nasal disease, or heating the bedroom. One most commonly employed method is humidification of the inspired air using an in line humidifier. Two types of humidifier are currently used. Cold pass-over humidifiers rely on humidifying the air through exposure to a large surface area of water. While they are cheap, the humidity output is low at high flows, typically 2 to 4 mg/L absolute humidity at flows above 25 L/min. The output is insufficient to prevent mucosal drying. Heated water bath humidifiers are more efficient, and produce high levels of humidity even at high flow rates. They are effective at preventing upper airway mucosal drying, prevent increases in nasal resistance, and are the most reliable means of treating upper airway symptoms.

Any of these active systems will have, to some degree or other, condensation (or rain out) in the tubing connecting the humidifier to the patient. The degree of condensation is strongly dependent on the ambient temperature, being much greater for greater differences between the ambient temperature and the gas temperature. The formation of large quantities of water in the breathing tubing causes considerable inconvenience to the patient, may accelerate cooling of the gas, may eventually occlude the tubing, or may be expelled into the patient. Also, the patient may experience discomfort, when breathing gases are delivered at temperatures widely divergent from that of the ambient temperature. Excessive condensation also results in inefficient usage of the water in the humidifying chamber.

In a hospital environment, where the ambient temperature of the atmosphere within the hospital environment is controlled by air conditioning for example, the required temperature for the humidified gases supplied by the apparatus may be controlled within set temperature parameters that are sufficiently close to the ambient temperature to prevent condensation within the conduit. However it is still necessary to have good control over the temperature and humidity of gases as they are actually supplied to the patient.

In the home care environment in which a user requires to use humidifying apparatus at home, the range of ambient and gas temperatures may well exceed that of the hospital environment. In the home care environment, the user will usually wear a facemask that is connected to end of the conduit and such a humidifier may be used in the home environment for the treatment of breathing and sleep apnea disorders and/or in conjunction with ventilators or CPAP devices. In addition, non-active humidifiers are commonly employed utilising the known pass over humidification technique.

For medical procedures where a patient's cavity is inflated for surgery, such as with laparoscopic or endoscopic surgery, it is important that gases entering the cavity are humid and at body temperature so as not to cause drying of the cavity tissues and to improve the recovery time of the patient.

In U.S. Pat. No. 5,640,951 issued to Fisher and Paykel a heated conduit for a humidified breathing assistance apparatus is disclosed which includes a temperature probe at the end of a heated conduit. By heating the conduit the problems relating to condensation in the conduit may be overcome. However in order to implement closed loop control over the temperature of the supplied gases (and therefore the power input to the conduit heating element 21), it is necessary to measure the temperature as close to the point at which it is supplied as possible. The temperature probe and its associated wiring included for this purpose make the attachment to the facemask or intubated patient bulky and therefore more uncomfortable for the patient Also for other medical procedures the probes and associated wiring also result in bulky attachments at the operation entry point causing obstructions to the surgeon or pressure sores around the point of entry.

WO01/13981 of Fisher & Paykel Healthcare Limited discloses a breathing assistance apparatus adapted to deliver humidified gases at a desired level of humidity to a patient, including a humidifier and a heated conduit The humidifier includes a controller, which determines a parameter of gas flow rate and then the required power input to the humidifier to deliver the gases to the patient at the required patient humidity. In a second embodiment, a conduit heating element is provided and the controller determines whether it has been correctly connected to the control. The heater plate of the humidifier is controlled to a particular temperature (set point) or the heater plate power is controlled through estimation or measurement of flow and/or ambient temperature. The heating element within the conduit is controlled by controlling the power to the heater through measurement or estimation of flow and ambient temperature. This eliminates the need for probes or external sensors. The blower or fan of this apparatus is pressure controlled for the purpose of treating CPAP. With this system the humidity of the gases supplied to the patient is not accurate, particularly at high flows.

DISCLOSURE OF THE INVENTION

It is an object of the present invention to provide a humidification system which goes some way to overcoming the abovementioned disadvantages or which at least provides the public or industry with a useful choice.

Accordingly in a first aspect the invention consists in a humidification system adapted to deliver humidified gases at a desired level of humidity, flow and temperature to a patient comprising:
(a) gases supply means providing a flow of gases,
(b) humidification means having an electrical input power and capable of humidifying said gases up to a level of humidity prior to delivery to said patient,
(c) flow measuring means that determines the flow of said gases before entry of said gases to said humidification means,
(d) humidity sensing means measuring the humidity of said gases before entry of said gases to said humidification means,
(e) first temperature sensing means measuring the temperature of the air external to said humidification system,
(f) transportation pathway means, having a heating means, said pathway means conveying said humidified gases from said humidification means to said patient, and
 (g) control means including stored instructions to:
  i) determine a transportation pathway heating means input power based on at least said temperature of said air as measured by said first temperature sensing means and said flow of said gases as measured by said flow measuring means,
  ii) determine a humidification means input power based on at least said flow of said gases as measured by said flow measuring means and said humidity of said gases as measured by said humidity sensing means to achieve said desired humidity, flow and temperature of said gases, which are to be supplied to said patient.

In a further aspect the invention consists in a humidification system adapted to deliver humidified gases at a desired level of humidity, flow and temperature to a patient comprising:
(a) gases supply means providing a flow of gases,
(b) humidification means having an electrical input power and capable of humidifying said gases up to a level of humidity prior to delivery to said patient,
(c) flow measuring means measuring the flow of said gases before entry of said gases to said humidification means,
(d) humidity sensing means measuring the humidity of said gases before entry of said gases to said humidification means,
(e) first temperature sensing means measuring the temperature of the air external to said humidification system,
(f) second temperature sensing means measuring the temperature of said water heating means,
(g) transportation pathway means, having a heating means, said pathway means conveying said humidified gases from said humidification means to said patient, and
 (h) control means including stored instructions to:
  i) determine a transportation pathway heating means input power based on at least said temperature of said air as measured by said first temperature sensing means and said flow of said gases as measured by said flow measuring means,
  ii) determine a required temperature of said water heating means based on at least said flow of said gases as measured by said flow measuring means and said humidity of said gases as measured by said humidity sensing means,
  iii) determine the actual temperature of said water heating means from said second temperature sensing means,
  iv) vary input power of said water heating means to cause said actual temperature to approach said required temperature to achieve said desired humidity, flow and temperature of said gases supplied to said patient.

In still a further aspect the invention consists in a humidification system adapted to deliver humidified gases at a desired level of humidity, flow and temperature to a patient comprising:
(a) gases supply means providing a flow of gases,
(b) humidification means having an electrical input power and capable of humidifying said gases up to a level of humidity prior to delivery to said patient and an inlet receiving said gases from said gases supply means and outlet to pass said gases to said patient,
(c) flow measuring means measuring the flow of said gases before entry of said gases to said humidification means,
(d) humidity sensing means measuring the humidity of said gases before entry of said gases to said humidification means,
(e) first temperature sensing means measuring the temperature of the air external to said humidification system,
(f) second temperature sensing means measuring the temperature of said gases passing out said outlet,
(g) transportation pathway means, having a heating means, said pathway means conveying said humidified gases from said humidification means to said patient, and
 (h) control means including stored instructions to:
  i) determine a transportation pathway heating means input power based on at least said temperature of said air as measured by said first temperature sensing means and said flow of said gases as measured by said flow measuring means,
  ii) determine a required temperature of said gases passing out said outlet based on at least said flow of said gases as measured by said flow measuring means and said humidity of said gases as measured by said humidity sensing means,
  iii) determine the actual temperature of said gases passing out said outlet from said second temperature sensing means,
  iv) vary input power of said water heating means to cause said actual temperature to approach said required temperature to achieve said desired humidity, flow and temperature of said gases supplied to said patient.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

Figure 1:
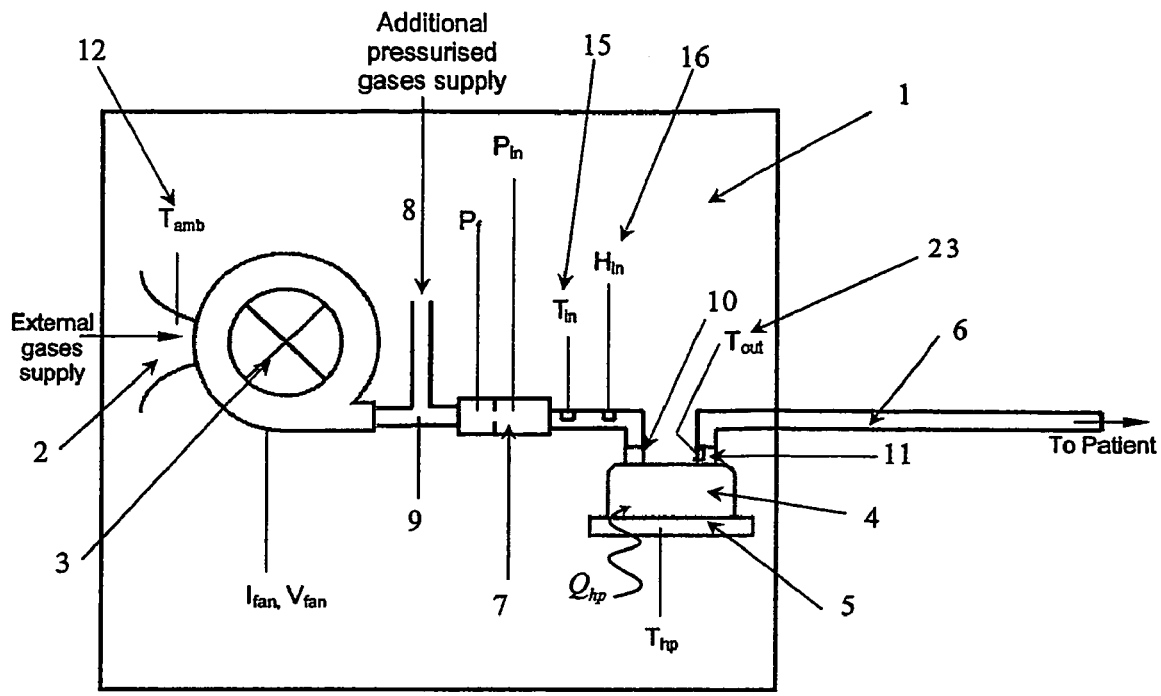
FIG. 1 is a schematic of the humidifier system of the present invention.

Whether used in a hospital environment or in a home care environment, the humidification system of the present invention will generally have associated with it a gases supply, such as ambient air, gases from cylinders, other compressed gas supply or gases from an insufflator, and a transport conduit from the humidification system to the patient, which is preferably heated to reduce condensation, or "rain out".

A heating element is preferably provided within the conduit to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heating element effectively replaces the energy lost from the gases through conduction and convection during transit through the conduit. Thus the conduit heating element ensures the gases delivered are at an optimal temperature and humidity.

The humidification system of the present invention may be used for various applications such as laparoscopic, ophthalmic or other surgical procedures, tracheostomised patients, and trans-tracheal insufflation. The humidification system of the present invention may be used in any treatments requiring or benefiting from the supply of a humidified gas supply.

The present invention provides a humidification system where the flow of gases passes in sequence through a flow driver (such as, a blower, fan, compressor or insufflator), humidification chamber and then heated delivery circuit. This system is contained such that the measurements made to control the flow, humidity and temperature of gases are internally sensed, so that there are no external sensors or electrical leads to components to hinder the patient or operator. This not only saves the cost of the extra sensors but also makes the system simpler and easier to set-up, operate and clean.

Typical blower humidifier combinations have been designed for the treatment of OSA and are pressure-controlled devices. They are also typically designed to be used as stand-alone blowers or in combination with a simple humidifier. These therefore typically deliver low levels of humidity i.e. 28 to 32 mg/L. The present invention is intended to deliver body temperature saturated gases (37° C. and 44 mg/L for room air) over a range of flows that would typically be used to provide for a patient's inspiratory flow requirements (that is, peak inspiratory flow).

The humidification system operates as a pressure limited, flow controlled device, so it adjusts the flow of gases to the level set by the patient Therefore, this system can be used to deliver humidified gas for patients with bypassed airways, such as tracheotomies or nasal cannula or masks or for other systems that require high flow gases. This has the potential to benefit many patients in both the home and hospital environments.

The humidification system of the present invention provides a much more accurate control of the delivered gas condition through estimation or measurement of any combination of flow, humidity, temperature and pressure, prior to the humidification chamber, and by use of the sensed ambient temperature. A subsequent calculation of the required heating element power, heater plate temperature set point and/or heater plate power can then be made to achieve optimal humidity, temperature and flow. Clinical data exists to suggest that gases at 37° C. and containing 44 mg of water vapour per litre at approximately atmospheric pressure are "optimal" for patient health.

The invention consists in a humidification system adapted to deliver humidified gases at a desired level of humidity, flow and temperature to a patient.

Referring to FIG. 1, the flow of gases through the humidification system 1 passes from the air within a room, through the inlet 2 (that may also include a filter or the like) into the internal fan unit 3 (blower or the like) then may be mixed with an additional pressurised gas supply 8 at junction 9 and then flow into humidification chamber 4 via an inlet port 10. In the preferred form of the humidification system the additional gas supply is mixed with the gases from the fan, but in other forms of the present invention no additional gas supply is provided.

Beneath the humidification chamber is a heater plate 5, which heats water held within the chamber 4. The gases exit the chamber 4 and pass out from the humidification system 1 to a heated delivery circuit 6 and to a patient (not shown). A controller (not shown) connects and controls all the components mentioned above and will be described in more detail below.

Figure 4:
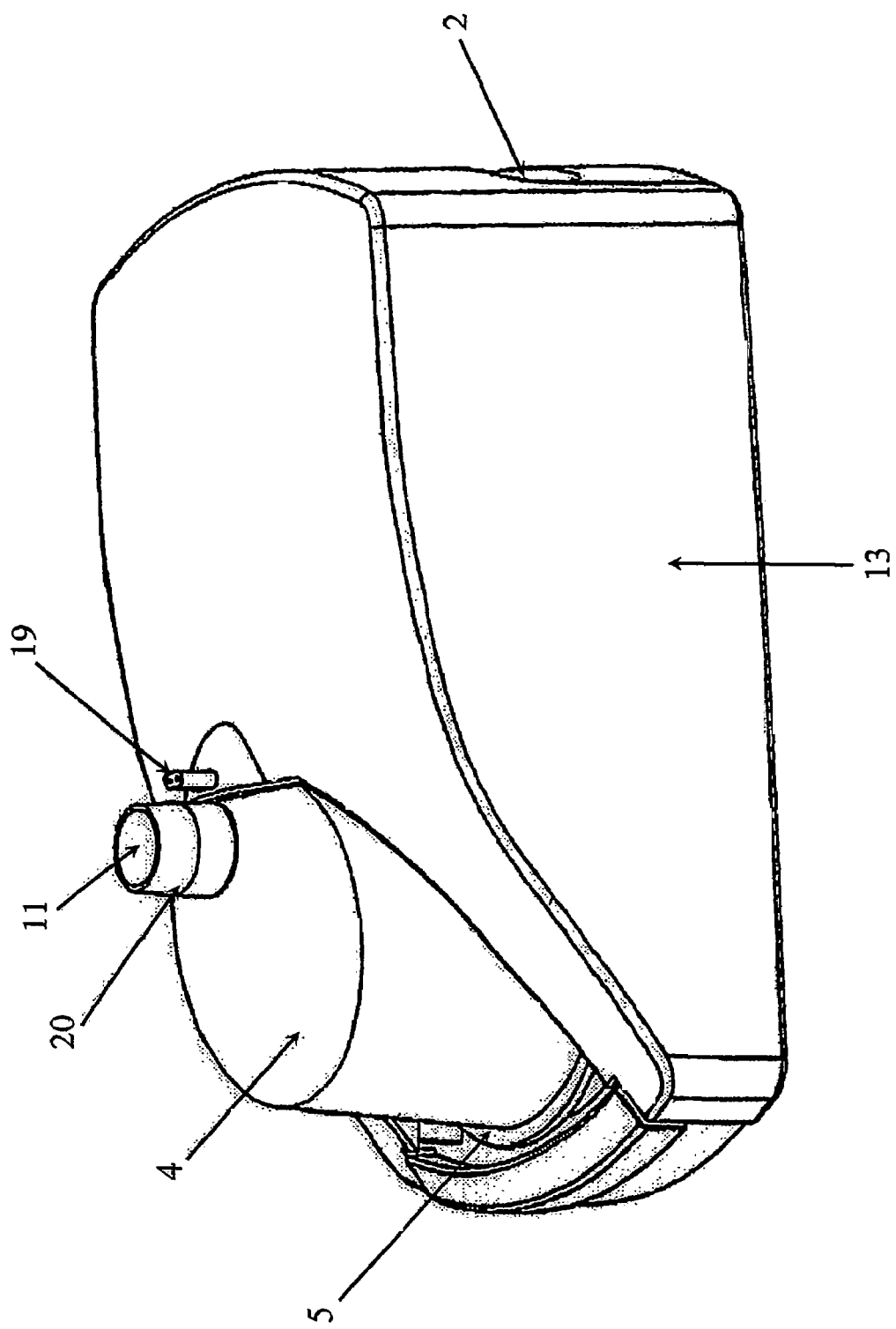
FIG. 4 is a perspective view of the humidification system of the present invention when housed in one housing.

Referring to FIGS. 1 and 4, in the preferred embodiment the fan unit 3 and humidifier, including chamber 4 and heater plate 5, and various controllers of these, are housed in one housing 13 and sensors, which are used to monitor various internal parameters of the fan, humidifier and gases, are internal within the housing 13, except for the external gas ambient air temperature sensor ($T_{amb}$) 12 that extends out slightly from the housing 13 so as to enable sensing of the ambient air surrounding the gases inlet 2.

In the preferred embodiment the humidification chamber extends out from the housing as shown in FIG. 4, and is capable in use of being removed and replaced by the patient or other user. Also, the inlet port 10 to the humidification chamber 4 is internal within the housing 13. The inlet 2 to the housing 13 where gases are drawn from the ambient air outside the housing 13 is located at the end of the housing 13, but in actuality may be located at any appropriate point in the housing 13. It must be appreciated that the embodiment described above in relation to the housing and FIG. 4 merely illustrate one form of the housing of the humidification system of the present invention.

In the preferred form of the present invention the fan 3 or flow source used within the humidification system is an electrically powered fan. Furthermore, it is preferred that the humidification chamber 4 sits atop an electrically powered heater plate 5 and an electrically powered heating element resides within the delivery circuit 6. These embodiments have been used for explanation purposes only. Any other suitable embodiment could have the same control scheme applied to it; for example, the fan could be replaced by a compressor, the chamber by a heated aerosol generator and the heater by a warm water jacket.

In the embodiment of the present invention as shown in FIGS. 1 to 4, an orifice plate 7 is used as the flow sensor and pressure sensor. The orifice plate allows for the measuring of the pressure of the gases after the gases leave the fan. From these measurements the velocity (flow) of the gases can be calculated. However, it must be appreciated in other forms of the present invention, other flow sensing devices such as a venturi or hotwire anemometer could be used. Furthermore, in other embodiments the flow sensor and pressure sensors taking measurements after the fan may actually be separate sensors.

Controlling the Flow of Gases

Referring again to FIG. 1, a portion or all of the total flow of gases through the humidification system 1 passes from the surrounding air within a room through the inlet 2 (that may also include a filter or the like) into the internal fan unit 3. Preferably the internal fan unit 3 is an electric fan, which blows external surrounding air through the humidification system. A portion of the total flow may be supplied from an additional pressurised gas supply 8, which mixes with the air at junction 9. Preferably the pressurised gas is oxygen, such that the air-oxygen mix delivered to the patient is rich in oxygen. Preferably the user is able to alter the concentration of oxygen.

Figure 2:
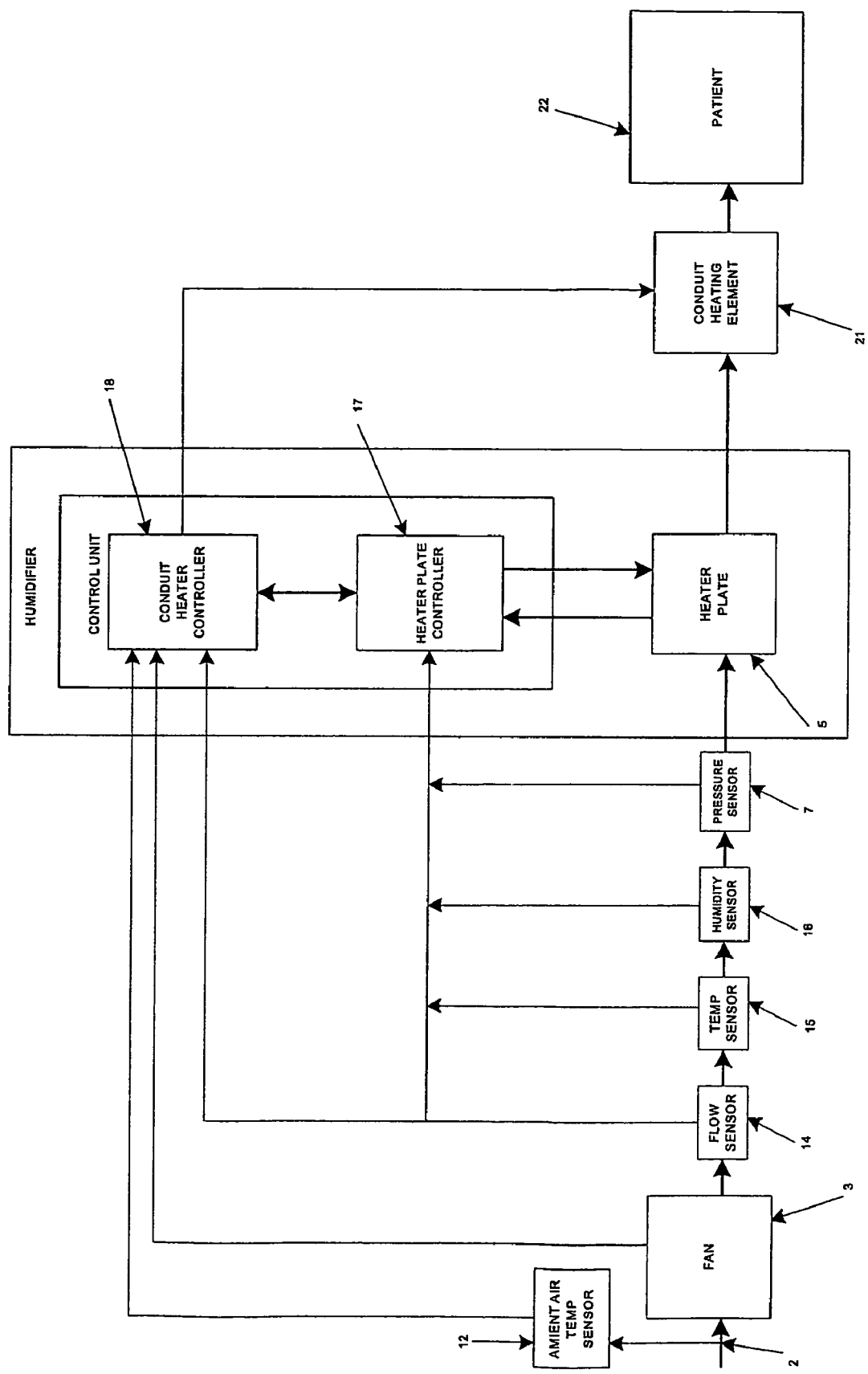
FIG. 2 is detailed block diagram of the humidification system of the present invention.

Referring to FIGS. 1 and 2, in the preferred embodiment the flow of gases through the humidification system 1 is measured by sensing the pressure on both sides of an orifice plate 7 situated as shown in FIG. 1 after the fan 3 outlet and orifice plate 7. The pressure on the fan 3 side of the orifice 7 is denoted $P_f$ and the pressure on the down stream side is denoted $P_{in}$. This method of flow sensing is well known in the art and the orifice plate can be calibrated to give an accurate flow measurement, termed measured flow. The fan speed $V_{fan}$ is then varied (by varying the power into the fan or the current to the fan $I_{fan}$) so that the measured flow of gases approaches the set flow as selected by the user.

Flow Sensor Checking

Correct operation of the flow sensor (orifice plate 7) can be monitored and checked by using less accurate flow estimation methods to find the operating flow range, if the flow sensor is outside of this range then the sensor is found to have failed. This improves safety and allows the device to be tolerant of some faults. The humidification system may be able to continue to operate or may cause an alarm to be signalled and the device to switch to a safe mode. The flow estimation method employed may be as described in WO 01/13981 of Fisher & Paykel Limited, the contents of which are herein incorporated, where the flow is estimated from the fan speed and the loading on the fan, or the flow can be estimated from the relationship between the sensed temperature of the heater plate and the power drawn by the heater plate.

Controlling the Level of Humidity of Gases—Heater Plate Control

Referring to FIGS. 1 and 2, the flow of gases through the humidification system 1 continues from the flow sensor 7, down a short conduit, past the temperature sensor and humidity sensor 16 into the humidifier chamber 4. The water within the humidification chamber 4 is in thermal contact with heater plate 5. The heating of the water directly affects the humidity output of the humidification chamber 4. Thus as the flow of gases pass out of the humidification chamber 4 exiting out the outlet port 11 the humidity level contained in the gases is affected by the electrical power input into the heating element (not shown) of the heater plate 5. Conversely, the humidity level contained within the gases is affected by the temperature of the water in the humidification chamber 4, or, as a result of, the temperature of the heater plate 5.

The humidity and flow of gases required to be delivered by the system to the patient is selected by the user, and thus the energy required to be delivered by the humidification means is known, as will be described below. The energy of the gases entering said humidification chamber 4 is also known from sensing flow, humidity and temperature by respectively using a flow sensor 14 (shown in FIG. 1 as the orifice plate 7), humidity sensor 16 and temperature sensor 15 before the humidification chamber 4. The basis of the humidity control employed in this invention is conservation of energy. The energy entering into and energy exiting from the humidification chamber 4 is known, therefore using conservation of energy principles the energy required to be added by the heater plate to ensure the required energy exits the humidification chamber 4 can be calculated.

In the preferred form of the humidification system the humidification chamber has a water autofeed mechanism that ensures the volume of water within the humidification chamber remains constant at all times. Furthermore, this autofeed mechanism ensures that the heat capacity of the water remains constant, which further simplifies the complexity of control required of the humidifier. An humidification chamber with autofeed capabilities that is suitable for this application is described in U.S. Pat. No. 5,445,143 of Fisher & Paykel Limited, the entire contents of which is incorporated herein. In this autofeed chamber the water level within the large volumes of cold water over a short period of time. This greatly affects the humidity output of the chamber.

The humidifier is in a very steady state with a constant flow of gases and small amounts of water steadily being added to a chamber with low thermal inertia. This steady state allows application of the steady flow energy equation. The amount of electrical power required to be supplied to the heater plate can be calculated as below.

$$\dot{Q}_{hp} = \dot{Q}_{out} - \dot{Q}_{in}$$

Where, $\dot{Q}_{out}$ is constant as specified by the user and $\dot{Q}_{in}$ is the enthalpy of the incoming gas stream, which is dependent upon the temperature and humidity of the incoming gas stream.

Therefore, $$\dot{Q}_{hp} = A + B \cdot H_{absolute} + C \cdot T_{in}$$

Where:
$\dot{Q}_{hp}$ = Heater plate power,
$\dot{Q}_{out}$ = Energy of gas passing out of chamber,
$\dot{Q}_{in}$ = Energy of gas passing into chamber,
$H_{absolute}$ = Absolute Humidity at inlet of humidification chamber,
$T_{in}$ = Gas temperature at inlet of humidification chamber,
A,B,C,D,E & F = Constants found experimentally for a specific flow and output humidity level, and
$T_{hp}$ = Heater plate temperature Alternatively the heater plate set point temperature can be calculated using:

$$T_{hp} = D + E \cdot H_{absolute} + F \cdot T_{in}$$

In this equation the constants take account of the thermal resistances within this specific system and are found experimentally.

The user selects the desired flow and humidity options to be delivered, for example 40 L/min & 44 mg/L, the heater plate controller 17 uses the constants known for this combination of options (i.e. D=96.37, E=−0.79, F=−0.22) and measures the temperature and humidity level of the gases coming into the humidification means (for example $T_{in}$=35° C., $H_{absolute}$=8.75 mg/L) then the heater plate temperature set point is calculated as below.

$$T_{hp} = 96.37 - 0.79 \cdot H_{absolute} - 0.22 \cdot T_{in}$$

$$T_{hp} = 96.37 - 0.79 \times 8.75 - 0.22 \times 35$$

$T_{hp}$=Heater plate temperature

Alternatively the heater plate set point temperature can be calculated using:

$$T_{hp}=D+E \cdot H_{absolute}+F \cdot T_{in}$$

In this equation the constants take account of the thermal resistances within this specific system and are found experimentally.

The user selects the desired flow and humidity options to be delivered, for example 40 L/min & 44 mg/L, the heater plate controller 17 uses the constants known for this combination of options (i.e. D=96.37, E=−0.79, F=−0.22) and measures the temperature and humidity level of the gases coming into the humidification means (for example $T_{in}$=35° C., $H_{absolute}$=8.75 mg/L) then the heater plate temperature set point is calculated as below.

$$T_{hp}=96.37-0.79 \cdot H_{absolute}-0.22 \cdot T_{in}$$

$$T_{hp}=96.37-0.79 \times 8.75-0.22 \times 35$$

$$T_{hp}=81.66° \text{ C.}$$

When there are gases at 35° C. containing 8.75 mg/L of water vapour, and these gases are flowing into the humidification chamber at 40 L/min, the heater plate temperature set point is calculated to be 82° C. When the sensed heater plate temperature approaches its set point the humidity output from the chamber approaches 44 mg/L.

It will be appreciated that a further embodiment of the invention could incorporate a sensor on the outlet of the humidification means to allow closed loop control as is known in the art. The novel concepts of the present invention could be incorporated to such a system to allow advances in the therapy. Many current humidifiers use temperature sensors or the like on the outlet, make an assumption that gases are close to saturated, and then control to a dry-bulb temperature set point. The assumption of saturation is incorrect for some inlet conditions, for example high inlet temperature or humidity, and this can cause the delivered absolute humidity to deviate widely from the desired or optimal level. This further embodiment of the present invention would operate under the common closed loop control method with the addition of a humidity sensor at the inlet of the humidification means. The information provided by such a sensor would allow an estimate of the correct dry-bulb temperature set point necessary to achieve the desired level of absolute humidity. Calculation of this set point would be similar in method and principle to the calculation described above. This humidification system of this embodiment would be considerably more reliable in its delivery of saturated gases than currently available humidifiers.

In particular, FIG. 1 shows such an additional temperature sensor 23 that may be provided at the outlet 11 to the humidifier chamber 4 to determine the temperature of the gases leaving the humidification chamber. The sensor $T_{out}$ 23 would preferably be provided within the outlet or humidifier housing, so that no external wiring leads to the sensor 23. This sensor 23 could be used in much the same manner as is described above to control humidity output. In fact, either the measurement of the heater plate temperature or temperature of the gases leaving the chamber could be used to control humidity output. In this case, the other of the two that is not being used to control humidity output could be used as a safety check which would switch the humidification system off if a temperature higher than a threshold was sensed.

Controlling Humidity and Temperature of Gases—Heated Delivery Circuit Control

As shown in FIGS. 1 and 2, the flow of gases exit the chamber 4 and pass out from the humidification system 1 to a heated delivery circuit 6 and to a patient 22. The heated delivery circuit 6 is a plastics conduit having a heated wire 21 extending through it, for example, such as that disclosed in any one of U.S. patent application Ser. Nos. 10/270,805 and 10/298,099, both of Fisher & Paykel Healthcare Limited, the contents of which are incorporated herein. The delivery conduit has wires extruded within the tubing walls. The conduit is extruded from an appropriate plastics material, such as a flexible polymer. The conduit has ridges or ribs extending from the surface of the conduit wall. Each rib extends towards the centre of the conduit and has a heating element, usually a wire that is embedded along the conduit's length. The heater wires may be made from copper, copper alloy or other appropriate electricity conducting material, such as a PTC heater. The heater wire is embedded within the ribs of the conduit by co-extrusion at the time the polymer conduit is extruded.

The heated delivery circuit 6 controls the temperature of the gases received by the patient 22. Both the temperature of the gases delivered to the patient, and the temperature of the gases at any point within the conduit are controlled. In order to transport the humidified gases produced from the humidification chamber the gases must be kept above the dew point temperature at any point within the delivery circuit in order to be able to transport all of the water vapour and avoid condensate. Referring to FIG. 2, the conduit heater controller 18 calculates the power required to be used to heat the delivery conduit 6 for a specific humidity setting and flow setting based off the ambient temperature $T_{amb}$ of the room. This ambient temperature is measured by the temperature sensor 12 (see FIG. 1) at the fan inlet 2 and enables the gauging of the amount of heat loss from the delivery conduit 6 to the surrounding ambient conditions. The relationship between said ambient temperature and the power used to heat the delivery conduit 6 in order to achieve the desired temperature at the patient is found experimentally.

Oxygen Mixing

Figure 3:
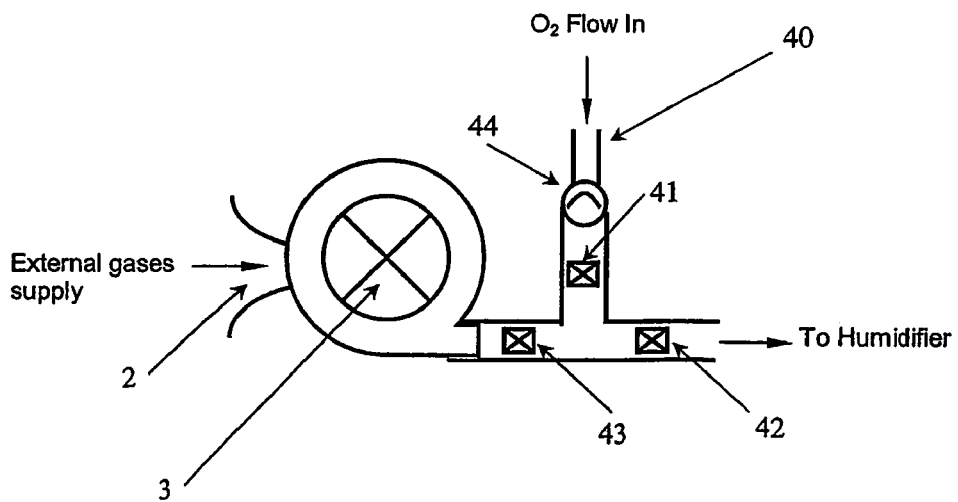
FIG. 3 is an illustration of the oxygen port of the humidification system of the present invention.

Referring to FIG. 3, the humidification system of the present invention in the preferred form incorporates an external port for the mixing of additional gases, preferably oxygen, into the gases flow. The port 40 is connected to a pressurised oxygen source and thereby causes oxygen to be added to the gases flow through the humidification system at a point before the humidifier, but after the fan 3.

It is usual to use a blender to mix the air and oxygen, however this requires both a compressed oxygen and air supply which is commonly not available, a blender is also expensive and thus adds a large additional cost. The other common method of mixing air and oxygen is an air entrainer. An air entrainer operates by using a high velocity jet of oxygen to shear past surrounding room air, which draws in some of this surrounding air and creates a mixed flow of gases down stream. The main disadvantage of an air entrainer is that if the downstream conduit has a large resistance to flow then the air entrainer is unable to generate a driving pressure to overcome this, and thus can't generate a flow. As the preferred embodiment of the present invention includes a long flexible conduit to deliver the gases to the patient, an air entrainer will not function in this circumstance.

In the preferred embodiment of the humidification system to measure the oxygen concentration of the gases flowing through the system either an oximeter (not shown) is provided in the mixed gas stream in a similar location to that of 42 or three flow meters 41, 42, 43, one each on the inward flowing oxygen stream 41, gases flow from the fan 43 and mixed gases flow 42 are provided. Any one of these three sensors are redundant for safety, the total flow and oxygen concentration can be calculated from any two of these sensors and should any one of these sensors fail these quantities are still known. As oxygen can be toxic in high concentrations it is important that this measurement is correct. It is displayed on the unit and clinical decisions may be made from this information. In order to allow for flexibility of the volume inputted into the gases flow, at the oxygen port 40 a needle valve 44 with a flow control knob is provided. This allows a user to alter the volume of the oxygen flow into the humidification system and ultimately the concentration of oxygen inspired by the patient.

Overheating Detection

The humidification system of the present invention includes within the conduit heater plate controller 18 a delivery conduit overheating detection system, such as that disclosed in U.S. patent application Ser. No. 10/270,805 of Fisher & Paykel Healthcare Limited, the contents of which are herein incorporated. Such a detection system for the heating element includes a method of detecting conduit overheating where, when the conduit is hot the current drawn by the heating element within the conduit exceeds a predetermined limit. The detection system ensures that the humidifier and conduit can be switched to a safe mode then back to an operating mode once the temperature of the heating element within the conduit has reduced to safe levels. The device comprises a sensor to detect the current in the heating element and controller that implements an algorithm to reduce the current in the heating element to a safe current region. If the conduit comprises two limbs the sensor detects the currents in each of the limbs determines the difference between these currents and if the difference approaches a predetermined limit then the power to each of the heating elements is reduced.

Electro Pneumatic Connector

In the preferred form of the humidification system of the present invention the delivery conduit 6 is connected to the output port 11 by way of an electro pneumatic connector, such as that described in U.S. patent application Ser. No. 10/452,448 of Fisher & Paykel Healthcare Limited, the contents of which is herein incorporated. In particular a connector of this type is utilised where the conduit has a heating element or electrical wire extending within, throughout and about it. The conduit is connected to the humidification chamber via a connector that provides both an electrical 19 and a pneumatic 20 coupling. In FIG. 4, only the chamber 4 side of a single port electro pneumatic connector is shown. In this form the single port connector is generally tubular and has a male and female portion where the pneumatic coupling is by a threaded, sliding collar or bayonet type connection that has an integral electrical port that provides power to the wire in the conduit.

We claim:

1. A humidification system adapted to deliver humidified gases at a desired level of humidity, flow and temperature to a patient comprising:
   (a) gases supply means providing a flow of gases,
   (b) humidification means having an electrical input power and capable of humidifying said gases up to a level of humidity prior to delivery to said patient,
   (c) flow measuring means that determines the flow of said gases before entry of said gases to said humidification means,
   (d) humidity sensing means measuring the humidity of said gases before entry of said gases to said humidification means,
   (e) first temperature sensing means measuring the temperature of the air external to said humidification system,
   (f) transportation pathway means, having a heating means, said pathway means conveying said humidified gases from said humidification means to said patient, and
   (g) control means including stored instructions to:
      i) determine a transportation pathway heating means input power based on at least said temperature of said air as measured by said first temperature sensing means and said flow of said gases as measured by said flow measuring means,
      ii) determine a humidification means input power based on at least said flow of said gases as measured by said flow measuring means and said humidity of said gases as measured by said humidity sensing means to achieve said desired humidity, flow and temperature of said gases, which are to be supplied to said patient.

2. A humidification system according to claim 1 wherein said humidification means comprises a humidification chamber adapted to receive a volume of water and water heating means to heat said water, said gases passing through said humidification chamber, through a gases inlet and out a gases outlet, and evaporating said water, said gases thereby being humidified.

3. A humidification system according to claim 1 or 2 wherein said humidification system further includes a second temperature sensing means measuring the temperature of said water heating means.

4. A humidification system adapted to deliver humidified gases at a desired level of humidity, flow and temperature to a patient comprising:
   (a) gases supply means providing a flow of gases,
   (b) humidification means having an electrical input power and capable of humidifying said gases up to a level of humidity prior to delivery to said patient,
   (c) flow measuring means measuring the flow of said gases before entry of said gases to said humidification means,
   (d) humidity sensing means measuring the humidity of said gases before entry of said gases to said humidification means,
   (e) first temperature sensing means measuring the temperature of the air external to said humidification system,
   (f) second temperature sensing means measuring the temperature of said water heating means,
   (g) transportation pathway means, having a heating means, said pathway means conveying said humidified gases from said humidification means to said patient, and
   (h) control means including stored instructions to:
      i) determine a transportation pathway heating means input power based on at least said temperature of said air as measured by said first temperature sensing means and said flow of said gases as measured by said flow measuring means,
      ii) determine a required temperature of said water heating means based on at least said flow of said gases as measured by said flow measuring means and said humidity of said gases as measured by said humidity sensing means, iii) determine the actual temperature of said water heating means from said second temperature sensing means, iv) vary input power of said water heating means to cause said actual temperature to approach said required temperature to achieve said desired humidity, flow and temperature of said gases supplied to said patient.

5. A humidification system according to claim 4 wherein said humidification system further includes a third temperature sensing means measuring the temperature of the gases before entry of said gases to said humidification means.

6. A humidification system according to claim 4 or 5 wherein said control means further includes instructions to determine said humidification means input power based on said flow of said gases as measured by said flow measuring means, said humidity of said gases as measured by said humidity sensing means, and said temperature of said gases as measured by said third temperature sensing means.

7. A humidification system according to claim 4 wherein said humidification system includes pressure sensing means measuring the pressure of said gases before entry of said gases to said humidification means.

8. A humidification system according to claim 4 wherein said control means further includes instructions to determine said humidification means input power based on said flow of said gases as measured by said flow measuring means, said humidity of said gases as measured by said humidity sensing means, said temperature of said gases as measured by said third temperature sensing means and said pressure of said gases as measured by said pressure sensing means.

9. A humidification system according to claim 4 wherein said humidification system includes an additional gases input port and at least one oxygen sensing means located in said flow of gases to measure said gases oxygen concentration.

10. A humidification system according to claim 9 wherein said additional gases input port allows for the addition of oxygen to said flow of gases through said humidification system.

11. A humidification system according to any of claims 9 or 10 wherein said control means further includes instructions to determine said humidification means input power based on said flow of said gases as measured by said flow measuring means, said humidity of said gases as measured by said humidity sensing means, said temperature of said gases as measured by said third temperature sensing means and said oxygen concentration of said gases as measured by said oxygen sensing means.

12. A humidification system according to claim 1 wherein said gases supply means, said humidification means, said flow measuring means, said humidity sensing means, said first and second temperature sensing means, said pressure sensing means and said control means are housed in one housing so that there are no external sensors and wiring extending from or on said humidification system to hinder said patient or other user of said humidification system.

13. A humidification system according to claim 12 wherein said housing has an external inlet for gases into said gases supply means and an outlet for said humidified gases, where said outlet is from said humidification chamber which is connected to said transportation pathway means by way of a connector that provides both an electrical and pneumatic connection between said humidification chamber and said transportation pathway.

14. A humidification system according to claim 4 wherein said humidification system includes transportation pathway means overheating detection for said heating means comprising: detecting means which include means to detect a current in said heating means, and detection control means which stores a program which causes the control means to:

i) receive input of said current in said heating means from said detecting means, and ii) if said current is below a safe current value, then reduce the power to said heating element from a operating current value to at least said safe current value, else return to i), iii) increase the power to said heating element after a predetermined time to said operating current value.

15. A humidification system according to claim 14 wherein said transportation pathway means is an extruded plastic tube, and said heating means is at least two conductive wires embedded within the wall of said tube to be partially or wholly contained within said wall.

16. A humidification system according to claim 15 wherein the cross sectional profile of said extruded plastic tube is such that total collapse or total occlusion is not possible during bending.

17. A humidification system according to claim 15 or 16 wherein said extruded plastic tube includes two or more co-extruded layers of differing plastic materials with varying properties.

18. A humidification system according to claim 4 wherein said heating means is a positive temperature co-efficient heating element, for example in a wire or tape form.

19. A humidification according to claim 4 wherein said humidification means includes a float valve system for controlling the level of liquid in a chamber comprising:

a valve body having an inlet for coupling to a liquid supply conduit and an outlet adapted to communicate with said chamber, a first valve seat formed in said body through which liquid must pass to reach said outlet, a second valve seat formed in said body located downstream of said first valve seat, through which liquid must pass to reach said outlet, first and second floats adapted to be disposed within said chamber, a first valve member actuated by said first float so as to close onto said first valve seat upon the first float assuming a position corresponding to a first predetermined level of liquid in said chamber, a second valve member actuated by said second float so as to close onto said second valve seat upon the second float assuming a position corresponding to a second predetermined level of liquid in said chamber, said second predetermined level of liquid being higher than said first predetennined level of liquid, a cylindrical actuating member connected to said second valve member in order to control displacement of said second valve member in response to said second float, an inner actuating member connected to said first valve member in order to control displacement of said first valve member in response to said first float, said inner actuating member being disposed within said cylindrical actuating member, said cylindrical actuating member and said inner actuating member independently connecting said first and second floats to respective valve members, and operable to allow free relative movement between said first and second valve members.

20. A humidification system according to claim 4 wherein said gases supply means is a fan driven by a variable speed electric motor.

21. A humidification system adapted to deliver humidified gases at a desired level of humidity, flow and temperature to a patient comprising:
   (a) gases supply means providing a flow of gases,
   (b) humidification means having an electrical input power and capable of humidifying said gases up to a level of humidity prior to delivery to said patient and an inlet receiving said gases from said gases supply means and outlet to pass said gases to said patient,
   (c) flow measuring means measuring the flow of said gases before entry of said gases to said humidification means,
   (d) humidity sensing means measuring the humidity of said gases before entry of said gases to said humidification means,
   (e) first temperature sensing means measuring the temperature of the air external to said humidification system,
   (f) second temperature sensing means measuring the temperature of said gases passing out said outlet,
   (g) transportation pathway means, having a heating means, said pathway means conveying said humidified gases from said humidification means to said patient, and
   (h) control means including stored instructions to:
      i) determine a transportation pathway heating means input power based on at least said temperature of said air as measured by said first temperature sensing means and said flow of said gases as measured by said flow measuring means,
      ii) determine a required temperature of said gases passing out said outlet based on at least said flow of said gases as measured by said flow measuring means and said humidity of said gases as measured by said humidity sensing means,
      iii) determine the actual temperature of said gases passing out said outlet from said second temperature sensing means,
      iv) vary input power of said water heating means to cause said actual temperature to approach said required temperature to achieve said desired humidity, flow and temperature of said gases supplied to said patient.

22. A humidification system according to claim 21 herein said gases supply means, said humidification means, said flow measuring means, said humidity sensing means, said first and second temperature sensing means, and said control means are housed in one housing so that there are no external sensors and wiring extending from or on said humidification system to hinder said patient or other user of said humidification system.

* * * * *